United States Patent [19]

Cavazza

[11] 4,382,092

[45] May 3, 1983

[54] PHARMACEUTICAL COMPOSITION COMPRISING GAMMA-BUTYROBETAINE FOR THE TREATMENT OF SYNDROMES INDUCED BY L-CARNITINE DEFICIENCY

[75] Inventor: Claudio Cavazza, Rome, Italy

[73] Assignee: Sigma-TAU Industrie Farmaceutiche Riunite S.p.A., Rome, Italy

[21] Appl. No.: 332,562

[22] Filed: Dec. 21, 1981

[30] Foreign Application Priority Data

Jan. 6, 1981 [IT] Italy ................................ 47518 A/81

[51] Int. Cl.$^3$ .......................................... A61K 31/205
[52] U.S. Cl. ................................................... 424/316
[58] Field of Search ......................................... 424/316

[56] References Cited

PUBLICATIONS

Chem. Abst. 94, (1981), 136862f.

*Primary Examiner*—Stanley J. Friedman
*Attorney, Agent, or Firm*—Ladas & Parry

[57] ABSTRACT

Further to the discovery that the syndromes induced by L-carnitine deficiency are provoked by defects in the gamma butyrobetaine biosynthesis in skeletal and heart muscles, whereas the liver and kidney of the patients exhibiting such syndromes retain unaltered their L-carnitine-making ability, there are disclosed a gamma-butyrobetaine-containing composition and a therapeutical method based on gamma-butyrobetaine administration for the treatment of such patients.

5 Claims, No Drawings

PHARMACEUTICAL COMPOSITION COMPRISING GAMMA-BUTYROBETAINE FOR THE TREATMENT OF SYNDROMES INDUCED BY L-CARNITINE DEFICIENCY

The present invention relates to a pharmaceutical composition comprising gamma-butyrobetaine and to a therapeutical method based on gamma-butyrobetaine administration for the treatment of patients exhibiting systemic and muscular L-carnitine deficiency syndromes, which for semplicity sake will be hereinbelow termed as "Carnitine-deficiency syndromes".

Gamma-butyrobetaine, $(CH_3)_3N—CH_2—CH_2—CH_2—COOH$, has never been previously used as therapeutical agent.

Gamma-butyrobetaine is the precursor of L-carnitine in the biosynthetic pathway of the latter compound. In fact, the researches carried out over the last years have permitted to definitely ascertain that the carnitine biosynthetic pathway is the following:

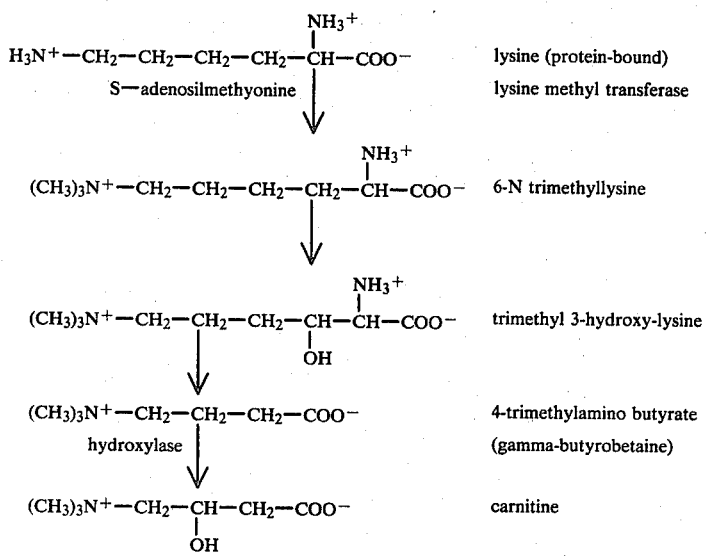

The chemical synthesis of gamma-butyrobetaine is well-known in the chemical art. A method for producing gamma-butyrobetaine is for instance disclosed in Can. J. Chem 54 (1976) 3310–3311. The teachings of this article are incorporated herein by reference.

The discovery that L-carnitine deficiency is the underlying factor of strikingly serious pathological conditions, particularly in young subjects, is comparatively recent. In fact, only in 1973 Engel and Angelini (Engel AG, Angelini C: Carnitine deficiency of human skeletal muscle associated with lipid storage myopathy: A new syndrome. Science 179: 899–902; 1973; Engel AG, Angelini C, Nelson AR: Identification of carnitine deficiency as a cause of human lipid storage myopathy. In Milhorat AT (Editor): Exploratory concepts: II Control mechanisms in development and function of muscle. Ambsterdam, Excerpta Medica) report an extremely low carnitine level in the skeletal muscles and an in vitro reduced oxidation of fatty acids by the muscle tissue of a 24-year-old woman affected from an unusual variety of lipid storage myopathy.

In 1975, Karpati et al (Neurology 25: 16–24, January 1975) report on a case of an 11-year-old boy affected from systemic carnitine deficiency. Because of his insufficient muscular development, the boy could only walk slowly, he was not able to run, jump and play normally. Both his body weight and height were markedly below normal values. The muscular tissue was assayed by electron microscopy and two populations of muscle cells were noted, one normal and one abnormal. The latter was characterized by the presence of an excess of lipid droplets and by abnormally abundant mitochondrial profiles. The boy was administered D,L-carnitine (2 grams per day) for 5 months. The carnitine levels in the muscular tissue, liver and plasma of both the patient and his parents are summarized in the following table.

|  | Carnitine Levels | | |
|---|---|---|---|
|  | Plasma (nanomoles/ml) | Muscle (nanomoles/mg of non-collagenous protein) | Liver (nanomoles/mg of non-collagenous protein) |
| Patient A | 7.9 | 0.50 | 0.73 |
| B | 19.4 | — | — |
| C | 57.0 | 0.48 | 1.02 |
| Mother | 32.8 | 13.24 | — |
| Father | 33.4 | 18.35 | — |

A: on regular diet.
B: on high meat and fish diet.
C: after five months of carnitine administration.

It can be noted that before carnitine administration the patient's muscular tissue contained traces only of carnitine, whereas in plasma and liver the carnitine level was reduced to about 12% of the average value.

Within two weeks from therapy beginning with carnitine, the patient showed a steady improvement of exercise tolerance, muscle strength, general well-being and appetite. After five months of D,L-carnitine administration, the foregoing parameters were all further improved and the patient was able to resume school full-time as well as playing and sport activities. However, whereas the carnitine plasma level had been restored to normal, the carnitine levels in the muscular tissues and liver were unaltered and his muscle bulk had only increased slightly to moderately.

The authors, after noticing that "the normal conversion of gamma-butyrobetaine to carnitine in vitro by the patient's liver appears to have ruled out a defect in the final step of the biosynthesis. A failure in any of the earliest steps of the biosynthetic pathway, however, would still be possible", conclude that "a primary biosynthetic defect, coupled with a secondary defect in storage or transport capacity, might explain all of our findings" (plasma and liver concentration markedly reduced before carnitine administration; muscular tissue and liver concentration not increased even after 5 months of carnitine administration, and this in spite of the normalization of plasma carnitine level).

Lastly, very recently A. G. Engel in Possible cause and effects of Carnitine deficiency in man: Carnitine Biosynthesis, metabolism and function. R. A. Frenkel and J. D. Mc. Garry (ed.) Academic Press, N.Y. 1980, hypothesizes that "if in man the kidneys were principally responsible of gamma-butyrobetaine synthesis and the main role of liver were that of hydroxylating this compound to carnitine, then a defective cellular up-take of gamma-butyrobetaine might cause a systemic carnitine deficiency". Also on the grounds of the hypothesys produced by this author it would not seem likely that gamma-butyrobetaine administration might improve the up-take of this compound and bring about the normalization of carnitine level in the muscular tissue of patients exhibiting carnitine deficiency syndromes.

It has now been found (and this is the presupposition of the present invention) that the L-carnitine deficiency syndromes are brought about by a defective biosynthesis in skeletal muscles and myocardium of gamma-butyrobetaine (the immediate precursor of L-carnitine in the biosynthesis of this latter compound), and not by the defective biosynthesis of 6-N trimethyl lysine or trimethyl 3-hydroxy-lysine, compounds which form from lysine in the previous biosynthesis steps.

It has also been surprisingly found that gamma-butyrobetaine administration to patients exhibiting L-carnitine deficiency syndromes (whose liver and kidneys retain, as known, the ability of converting gammabutyrobetaine into L-carnitine) permits to restore to normal, after a certain treatment period, not only the L-carnitine plasma levels, but also the tissue levels, particularly those of the skeletal muscles.

The gist of the present invention is, therefore, the use of gamma-butyrobetaine as therapeutical agent in the treatment of patients exhibiting L-carnitine deficiency syndromes.

More particularly, the present invention concerns an orally or parenterally administrable pharmaceutical composition for the treatment of patients exhibiting L-carnitine deficiency syndromes, which comprises a therapeutically effective amount of gamma-butyrobetaine and a pharmacologically acceptable excipient. This pharmaceutical composition will comprise, when in unit dosage form, from about 25 to about 1000 mg of gamma-butyrobetaine.

The present invention also encompasses a therapeutical method for the treatment of patients exhibiting L-carnitine deficiency syndromes, which comprises the oral or parenteral administration to patients in need thereof of a therapeutically effective amount of gamma-butyrobetaine. This therapeutically effective amount of gamma-butyrobetaine will be selected in such a way as to be sufficient to biosynthetically produce in said patients an amount of L-carnitine corresponding to normal plasma and tissue levels.

In practice, about 2–20 mg of gamma-butyrobetaine/Kg of body weight/day will be orally or parentally administered, although smaller or larger doses than those indicated can be administered utilizing sound professional judgement having regard to the age, weight, general conditions and pathological status of the treated patient.

Gamma-butyrobetaine is compounded in any of the usual pharmaceutical forms suitable for oral or parenteral administration which are prepared by conventional procedures well-known to those having ordinary skill in the pharmacological techniques. These forms include oral unit dosage forms, both solid and liquid, such as for instance tablets, capsules, solutions, syrups and the like, and injectable forms such as for instance sterile solutions for ampoules and phials.

The use of gamma-butyrobetaine in the treatment of L-carnitine deficiency syndromes entails a further, economically remarkable advantage over the use of L-carnitine in addition to the previously mentioned effect of restoring to normal the L-carnitine levels in the muscular tissue also. In fact, the industrial preparation of gamma-butyrobetaine is less complicated and expensive than L-carnitine preparation. The L-carnitine preparation requires the optical antipode resolution of the racemic mixture which is unavoidably obtained in the chemical synthesis of carnitine, whilst the enzyme processes so far proposed are not satisfactory yet, particularly when applied on an industrial scale.

What is claimed is:

1. An orally or parenterally administrable pharmaceutical composition for the treatment of patients exhibiting L-carnitine deficiency syndromes, which comprises a therapeutically effective amount of gamma-butyrobetaine and a pharmacologically acceptable excipient.

2. The pharmaceutical composition of claim 1, in unit dosage form, which comprises from about 25 to about 1000 mg of gamma-butyrobetaine.

3. A therapeutical method for the treatment of patients exhibiting L-carnitine deficiency syndromes, which comprises orally or parenterally administering to said patients a therapeutically effective amount of gamma-butyrobetaine.

4. The therapeutical method of claim 4, wherein said therapeutically effective amount of gamma-butyrobetaine is sufficient to biosynthetically produce in said patients an L-carnitine amount corresponding to normal plasma and tissue levels.

5. The therapeutical method of claim 5, which comprises orally or parenterally administering to said patients a gamma-butyrobetaine amount comprised between about 2 and about 20 mg/Kg of body weight/day.

* * * * *